(12) United States Patent
Nakae et al.

(10) Patent No.: US 9,399,656 B2
(45) Date of Patent: Jul. 26, 2016

(54) COMPOUND, METHOD FOR PRODUCING SAME, AND USE OF SAME

(71) Applicant: Microbial Chemistry Research Foundation, Tokyo (JP)

(72) Inventors: Koichi Nakae, Tokyo (JP); Fukiko Kojima, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 87 days.

(21) Appl. No.: 14/264,361

(22) Filed: Apr. 29, 2014

(65) Prior Publication Data

US 2014/0256923 A1    Sep. 11, 2014

Related U.S. Application Data

(63) Continuation of application No. PCT/JP2012/070821, filed on Aug. 16, 2012.

(30) Foreign Application Priority Data

Oct. 31, 2011 (JP) ................................. 2011-238848

(51) Int. Cl.
*C07H 15/22* (2006.01)
*C07H 15/20* (2006.01)
*C12P 17/06* (2006.01)
*C12R 1/01* (2006.01)
*C12P 19/48* (2006.01)

(52) U.S. Cl.
CPC ................ *C07H 15/22* (2013.01); *C07H 15/20* (2013.01); *C12P 17/06* (2013.01); *C12P 19/48* (2013.01); *C12R 1/01* (2013.01)

(58) Field of Classification Search
None
See application file for complete search history.

(56) References Cited

FOREIGN PATENT DOCUMENTS

| EP | 1 477 472 | 11/2004 |
|---|---|---|
| JP | 2003-192588 | 7/2003 |
| JP | 2004-262868 | 9/2004 |
| JP | 2007-326864 | 12/2007 |
| JP | 2009-167217 | 7/2009 |

OTHER PUBLICATIONS

Nakae Koichi et al, "Study on Novel Prostaglandin Release Inhibitor Pronqodine A Obtained from Metabolite of Actinomycete," Proceedings of Annual Meeting of Japan Society for Bioscience, Biotechnology and Agrochemistry, Mar. 5, 2011, p. 18 (2A05a06).

*Primary Examiner* — Travis C McIntosh, III
(74) *Attorney, Agent, or Firm* — Carmody Torrance Sandak & Hennessey LLP

(57) ABSTRACT

A compound represented by the following Structural Formula (A) or a salt thereof. The compound or the salt thereof is suitably produced from a microorganism belonging to the genus *Saccharothrix* and can be suitably used as a prostaglandin production inhibitor.

Structural Formula (A)

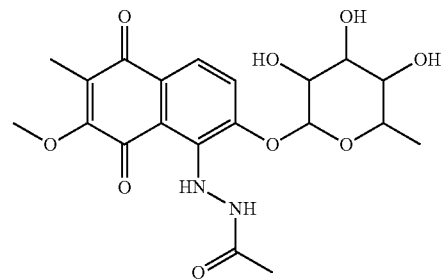

2 Claims, 5 Drawing Sheets

COMPOUND, METHOD FOR PRODUCING SAME, AND USE OF SAME

CROSS-REFERENCE TO RELATED APPLICATION

This application is a continuation application of International Application PCT/JP2012/070821 filed on Aug. 16, 2012 and designated the U.S., the entire contents of which are incorporated herein by reference.

BACKGROUND OF THE INVENTION

1. Field of the Invention

The present invention relates to a novel compound having a prostaglandin production inhibitory action, a method for producing the novel compound, a novel microorganism which is a microorganism producing the novel compound, a compound-containing composition containing the novel compound, and a prostaglandin production inhibitor containing the compound-containing composition.

2. Description of the Related Art

Prostaglandin (PG) is a bioactive substance which is a metabolite of arachidonic acid released from a cell membrane. Known types of prostaglandin include $PGE_2$, $PGD_2$, $PGF_{2\alpha}$, and $PGI_2$. When a living body receives physical stimulation or inflammatory irritation, the living body produces the prostaglandin, which binds to a specific receptor thereof to thereby cause various physiological responses in the living body.

Examples of the physiological responses include inflammation reactions such as pruritus, fever, vascular hyperpermeability, and pain; abnormal enhancement of sensory nerve, bronchial smooth muscle contraction, platelet aggregation, tumor-cell proliferation, bone resorption promotion, and neuron degeneration. Therefore, the prostaglandin plays a key role in manifestation or pathogenesis in various diseases such as asthma, a cardiovascular disease, preterm delivery, nephritis, atherosclerosis, overactive bladder, chronic rheumatoid arthritis, osteoarthritis, and cancer.

Therefore, it has been expected that the various diseases can be prevented or treated by inhibiting production of the prostaglandin.

Various compounds inhibiting production of the prostaglandin have been proposed (see, for example, Japanese Patent Application Laid-Open (JP-A) Nos. 2007-326864, 2009-167217, and 2004-262868). However, these compounds have an unsatisfactory prostaglandin production inhibitory action.

Thus, at present, keen demand has arisen for a novel compound which has an excellent prostaglandin production inhibitory action, which can be used for preventing or treating various diseases caused by prostaglandin, and which has high safety.

SUMMARY OF THE INVENTION

The present invention aims to solve the above existing problems and achieve the following objects. Specifically, an object of the present invention is to provide a novel compound which has an excellent prostaglandin production inhibitory action, which can be used for preventing or treating various diseases caused by prostaglandin, and which has high safety; a method for producing the novel compound; a novel microorganism which is a microorganism producing the novel compound; a compound-containing composition containing the novel compound; and a prostaglandin production inhibitor containing the compound-containing composition.

In order to solve the above existing problems, the present inventors conducted extensive studies. Specifically, the present inventors isolated microorganisms from soils in various regions, and examined metabolites produced by the isolated microorganisms. As a result, they have found that a newly isolated microorganism belonging to the genus *Saccharothrix* produces a substance exhibiting a prostaglandin production inhibitory action in a culture medium. They isolated an active ingredient from the culture medium and purified, and then examined for its physico-chemical properties. Accordingly, they have found that the resultant active ingredient is a compound represented by the following Structural Formula (A) which is different from any known substance and which has a prostaglandin production inhibitory action. The present invention has been accomplished on the basis of these findings.

The present invention is based on the above findings obtained by the present inventors. Means for solving the problems is as follows.

A compound represented by the following Structural Formula (A) or a salt thereof:

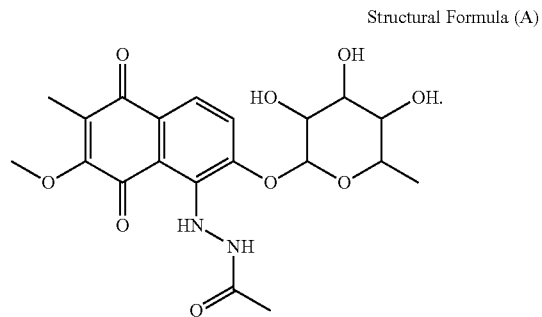

Structural Formula (A)

The present invention can provide a novel compound which has an excellent prostaglandin production inhibitory action, which can be used for preventing or treating of various diseases caused by prostaglandin, and which has high safety; a method for producing the novel compound; a novel microorganism which is a microorganism producing the novel compound; a compound-containing composition containing the novel compound; and a prostaglandin production inhibitor containing the compound-containing composition. These can solve the above existing problems and achieve the above object.

DETAILED DESCRIPTION OF THE INVENTION (Novel Compound)

A compound of the present invention is a compound represented by the following Structural Formula (A) which is a novel compound isolated by the present inventors.

The compound represented by the following Structural Formula (A) is a novel substance which is distinct from any known compound in physico-chemical properties and structural characteristics described below:

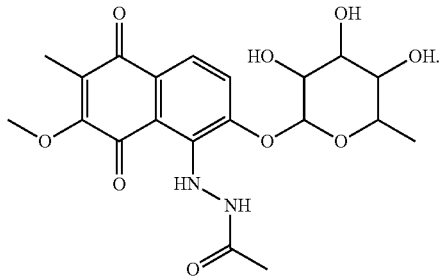

Structural Formula (A)

<Physico-Chemical Properties>

Figure 1:
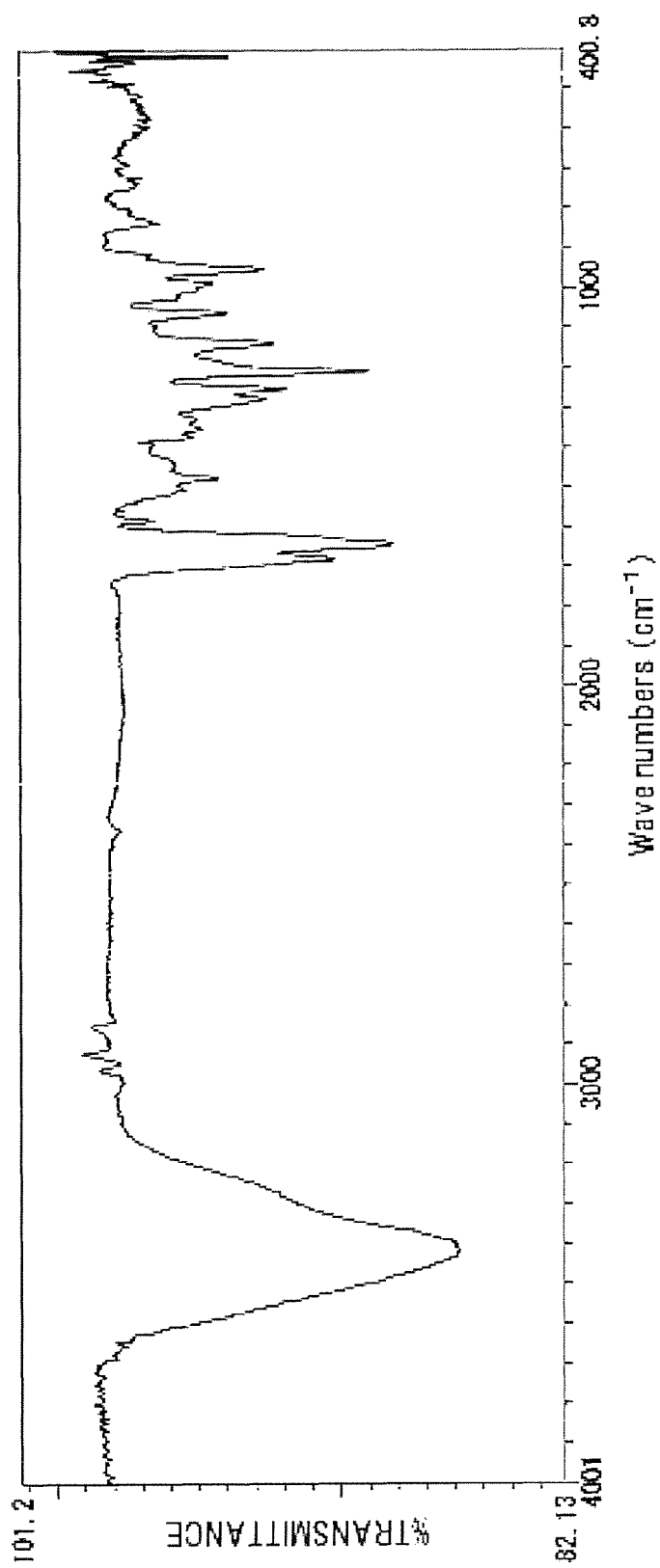
FIG. 1 is an infrared absorption spectrum of a compound of the present invention measured by the KBr method.
Figure 2:
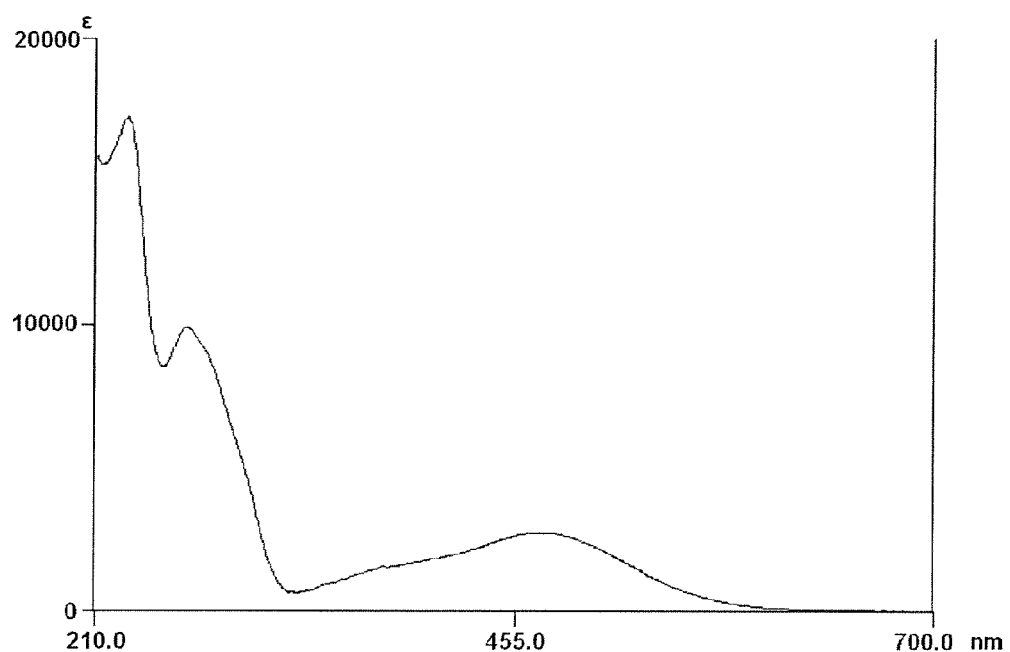
FIG. 2 is a UV absorption spectrum of a compound of the present invention measured in methanol.
Figure 3:
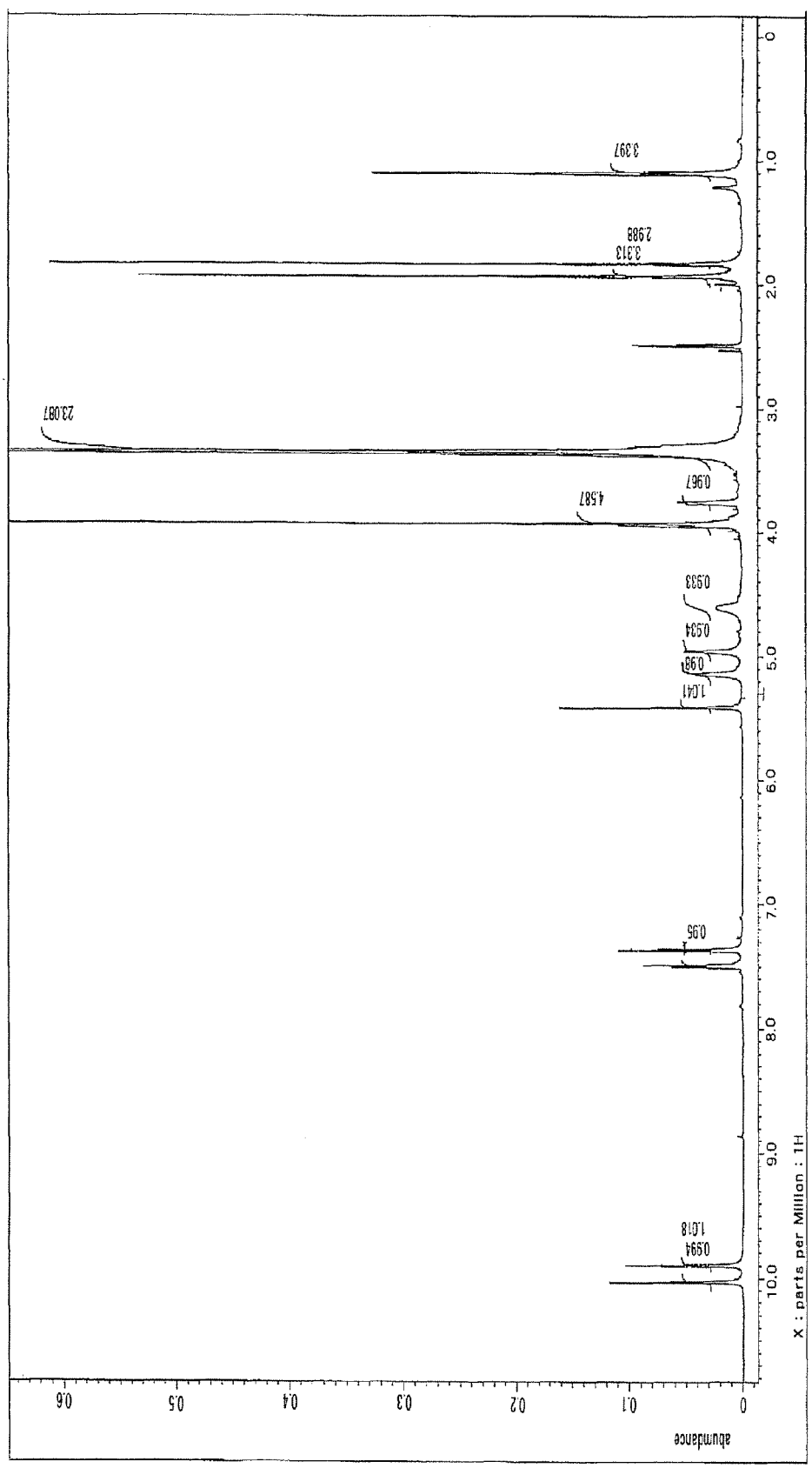
FIG. 3 is a $^1H$ nuclear magnetic resonance spectrum of a compound of the present invention measured in deuterated dimethyl sulfoxide (deuterated DMSO).
Figure 4:
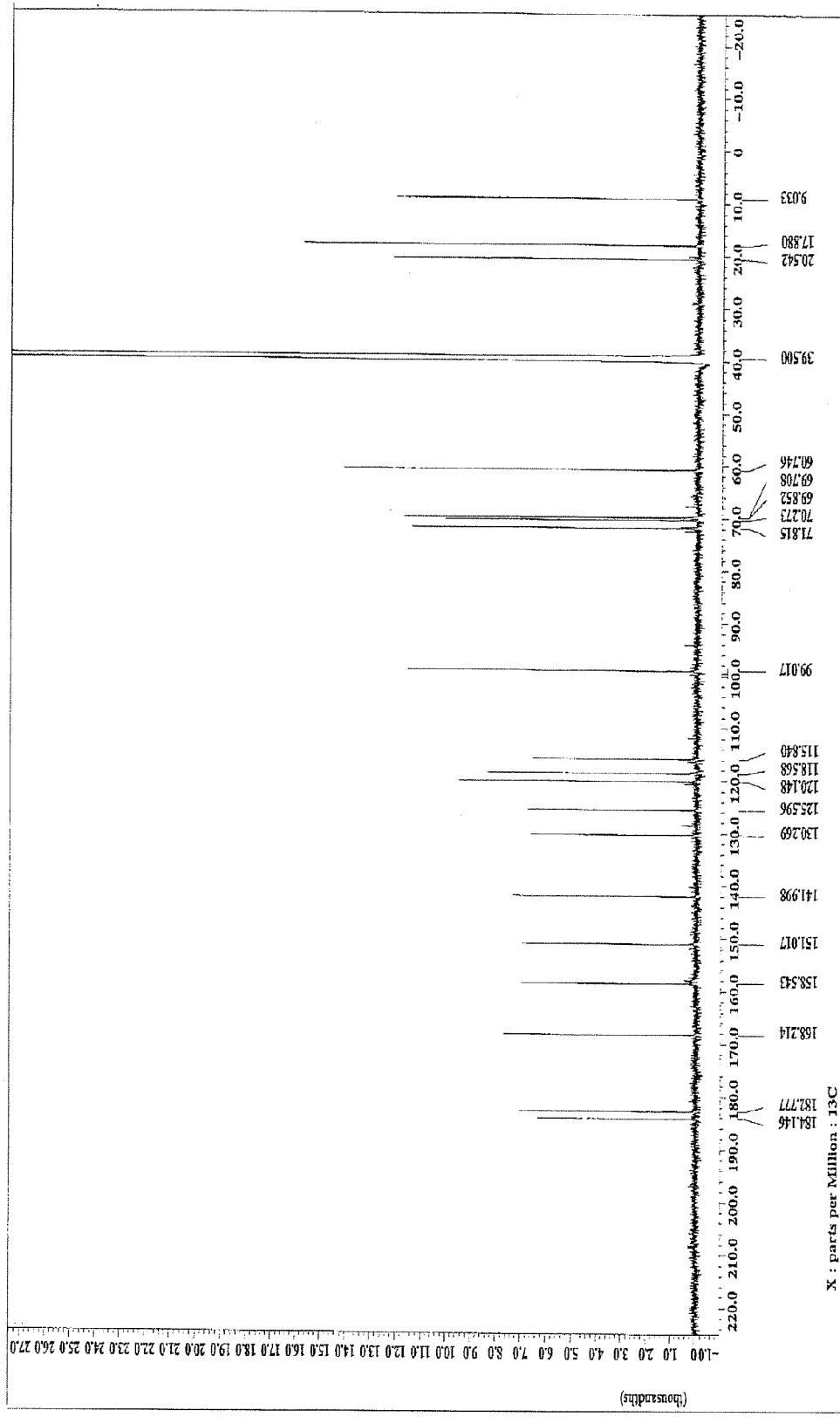
FIG. 4 is a $^{13}C$ nuclear magnetic resonance spectrum of a compound of the present invention measured in deuterated DMSO.

Physico-chemical properties of the compound represented by the Structural Formula (A) are as follows.
(1) Appearance: reddish violet powder
(2) Molecular formula: $C_{20}H_{24}N_2O_9$
(3) High resolution mass spectrometry (HRESIMS: positive ion mode)
    Found: m/z 459.1371 $(M+Na)^+$
    Calcd: m/z 459.1374 (as $C_{20}H_{24}N_2O_9Na$)
(4) Specific rotation $[\alpha]D^{23}=-358°$ (c 0.0036, methanol)
(5) Infrared absorption spectrum measured by the KBr method: as shown in FIG. 1
(6) UV absorption spectrum measured in methanol: as shown in FIG. 2
    $\lambda_{max}$ nm ($\epsilon$): 263 (9,909), 470 (2,739)
(7) Proton nuclear magnetic resonance (NMR) spectrum measured at 600 MHz in deuterated DMSO at 25° C.: as shown in FIG. 3
(8) $^{13}C$ nuclear magnetic resonance spectrum measured at 150 MHz in deuterated DMSO at 25° C.: as shown in FIG. 4

Whether a compound has a structure represented by the Structural Formula (A) can be confirmed by appropriately selected various analysis methods. For example, it can be confirmed through analysis of the mass spectrometry, the infrared absorption spectrum, the UV absorption spectrum, the proton nuclear magnetic resonance spectrum, or the $^{13}C$ nuclear magnetic resonance spectrum.

The novel compound of the present invention may be a salt of the compound represented by the Structural Formula (A).

The salt is not particularly limited and may be appropriately selected depending on the intended purpose, as long as it is a pharmaceutically acceptable salt. Examples thereof include organic salts such as acetate or citrate, hydrochloride, and carbonate.

The compound represented by the Structural Formula (A) may be obtained from a microorganism producing the compound represented by the Structural Formula (A), or may be obtained through chemical synthesis. However, the compound is preferably obtained by the below-described method for producing a compound of the present invention.

<Application>

The compound represented by the Structural Formula (A) is a compound having an excellent prostaglandin production inhibitory action and high safety. Therefore, the compound represented by the Structural Formula (A) can be suitably used as an active ingredient of a compound-containing composition of the present invention or a prostaglandin production inhibitor of the present invention described below.

(Method for Producing Compound)

A method for producing a compound of the present invention is a method for producing the compound represented by the Structural Formula (A). The method includes a culturing step and an isolation step; and, if necessary, further includes other steps.

<Culturing Step>

The culturing step is a step of culturing a microorganism belonging to the genus *Saccharothrix* and being capable of producing the compound represented by the Structural Formula (A).

The microorganism is not particularly limited and may be appropriately selected depending on the intended purpose, as long as it belongs to the genus *Saccharothrix* and is capable of producing the compound represented by the Structural Formula (A).

Whether the microorganism is capable of producing the compound represented by the Structural Formula (A) can be determined by, for example, a method in which an ingredient contained in a culture, preferably in a culture supernatant of the microorganism is measured for a prostaglandin production inhibitory action, or a method in which the compound represented by the Structural Formula (A) is detected through various analysis methods.

In the case where the prostaglandin production inhibitory action is measured, the microorganism can be determined as being capable of producing the compound represented by the Structural Formula (A) when the culture of the microorganism has the prostaglandin production inhibitory action.

Specifically, the culture is added to a cultured cell of, for example, human, and prostaglandin (e.g., 6-keto-prostaglandin $F_{1\alpha}$ which is a stabilized metabolite of prostaglandin $E_2$ or prostaglandin $I_2$) produced in the culture is detected. When the prostaglandin production is inhibited, the culture of the microorganism can be determined as having the prostaglandin production inhibitory action.

Specific example of the microorganism includes a microorganism of *Saccharothrix* sp. MI559-46F5 strain (accession number: NITE BP-01152) which was isolated by the present inventors. Also, other strains that are capable of producing the compound represented by the Structural Formula (A) can be isolated from the natural world by a routine method. Note that, through mutation treatments such as exposure to radiation, the microorganism of *Saccharothrix* sp. MI559-46F5 strain and other microorganisms capable of producing the compound represented by the Structural Formula (A) can be mutated so that they have increased production capability of the compound represented by the Structural Formula (A). Moreover, the compound represented by the Structural Formula (A) can be produced through genetically engineering techniques.

The culturing is performed as follows. Specifically, a microorganism producing the compound represented by the Structural Formula (A) (hereinafter may be simply referred to as "compounds-producing microorganism") is inoculated into a nutrient medium (hereinafter may be simply referred to as "medium") and cultured at a temperature suitable for producing the compound represented by the Structural Formula (A).

The nutrient medium is not particularly limited and may be appropriately selected depending on the intended purpose. For example, known nutrient media which are conventionally used for culturing actinomycetes can be used. The nutrient medium may be a liquid medium or an agar medium.

A nutrient source to be added to the nutrient medium is not particularly limited and may be appropriately selected depending on the intended purpose. Examples thereof include nitrogen sources such as commercially available soy flour, peptone, yeast extract, meat extract, corn steep liquor, and ammonium sulfate; and carbon sources such as fats and carbohydrates, e.g., tomato paste, glycerin, starch, glucose, galactose, dextrin, and BACTO SOYTONE. In addition, inorganic salts such as sodium chloride and calcium carbonate may be added to the medium before use. If necessary, a trace amount of a metal salt may be added to the medium before use.

Any known material for culturing the compound represented by the Structural Formula (A) may be used so long as the material can be utilized by the compounds-producing microorganism to promote the production of the compound represented by the Structural Formula (A).

A seed used for producing the compound represented by the Structural Formula (A) is not particularly limited and may be appropriately selected depending on the intended purpose. For example, a culture obtained through culturing of the compounds-producing microorganism on an agar medium or a slant medium may be used.

A method for culturing is not particularly limited and may be appropriately selected depending on the intended purpose. However, the culturing is preferably performed under an aerobic condition.

The culturing temperature is not particularly limited and may be appropriately selected depending on the type of the compounds-producing microorganism, so long as the growth of the compounds-producing microorganism is not substantially inhibited and the compounds-producing microorganism can produce the compound represented by the Structural Formula (A). The culturing temperature is preferably 25° C. to 35° C.

The culturing period is not particularly limited and may be appropriately selected depending on the accumulation of the compound represented by the Structural Formula (A).

<Isolation Step>

The isolation step is a step of isolating the compound represented by the Structural Formula (A) from the culture obtained from the culturing step. The compound represented by the Structural Formula (A) has the above-described physico-chemical properties, so that the compound represented by the Structural Formula (A) can be isolated from the culture according to the properties. As used herein, "isolation" means that the compound represented by the Structural Formula (A) is separated and/or purified from the culture.

The culture is not particularly limited and may be appropriately selected depending on the intended purpose, as long as it is obtained from the culturing step and contains the compound represented by the Structural Formula (A). Examples thereof include a microbial body, a culture supernatant, and a mixture thereof. Among them, the culture is preferably a culture supernatant because the compound represented by the Structural Formula (A) can be efficiently obtained.

Note that, in the case where the culture is the microbial body, the compound represented by the Structural Formula (A) may be extracted from the microbial body by, for example, an extraction method using an appropriate organic solvent or an elution method including crushing the microbial body, followed by subjecting to separation and/or purification.

A method for isolating is not particularly limited and may be appropriately selected from methods used for isolating metabolites produced by microorganisms. Examples thereof include a solvent extraction method, a method utilizing a difference in adsorption affinities against various adsorbents, and a chromatographic method. These methods may be used alone or appropriately combined, and optionally used repeatedly to separate and/or purify the compound represented by the Structural Formula (A).

A solvent used for the solvent extraction method is not particularly limited and may be appropriately selected depending on the intended purpose. Examples thereof include ethyl acetate and n-butanol.

The adsorbent is not particularly limited and may be appropriately selected from known adsorbents depending on the intended purpose. Example thereof includes a polystyrene-based adsorptive resin.

Specific examples of commercially available products of the adsorbent include AMBERLITE XAD (manufactured by Rohm and Haas Company) and DIAION HP-20 (manufactured by Mitsubishi Chemical Corporation).

The chromatographic method is not particularly limited and may be appropriately selected depending on the intended purpose. Examples thereof include a thin-layer chromatographic method, and a preparative high-performance liquid chromatographic method (preparative HPLC) using a normal-phase or reverse-phase column.

A carrier used for the chromatographic method is not particularly limited and may be appropriately selected depending on the intended purpose. Examples thereof include a gel filtration, silica gel, alumina, and activated carbon.

Specific examples of commercially available products of the carrier used for the gel filtration chromatographic method include TOYOPEARL HW-40F (manufactured by TOSOH CORPORATION) and SEPHADEX LH-20 (manufactured by General Electric Company).

A method for eluting the compound represented by the Structural Formula (A) from the adsorbent or the carrier used in the chromatographic method is not particularly limited and may be appropriately selected depending on the type or the property of the adsorbent or the carrier. For example, in the case of the polystyrene-based adsorptive resin, an elution method using hydroalcohol or aqueous acetone as an elution solvent may be used.

As described above, the compound represented by the Structural Formula (A) can be produced. Thus, the compound represented by the Structural Formula (A) can be suitably obtained.

<Other Step>

The other step is not particularly limited and may be appropriately selected depending on the intended purpose. Examples thereof include a washing step which is a step of washing the culture obtained from the culturing step or the compound represented by the Structural Formula (A) obtained from the isolation step, and a purification step which is a step of purifying the compound represented by the Structural Formula (A) obtained from the isolation step. The washing step and the purification step are appropriately performed by any of known methods.

(Microorganism)

A microorganism of the present invention belongs to the genus *Saccharothrix* and is capable of producing the compound represented by the Structural Formula (A). The microorganism is capable of producing the compound represented by the Structural Formula (A), so that the microorganism is not particularly limited and may be appropriately selected depending on the intended purpose, as long as it is a microorganism which can be used as the microorganism producing the compound represented by the Structural Formula (A) in the method for producing the compound of the present invention.

Among such microorganisms, the microorganism given accession number MI559-46F5 strain is particularly preferably used. Note that, the MI559-46F5 strain was deposited under accession number NITE P-1152 on Sep. 28, 2011 by Incorporated Administrative Agency National Institute of Technology and Evaluation Patent Microorganisms Depositary (2-5-8 Kazusakamatari, Kisarazu-shi, Chiba 292-0818, Japan). After that, a request of transfer to international deposit under the Budapest Treaty was accepted, and it was deposited under accession number NITE BP-01152 as international deposit.

Note that, as with other microorganisms, the MI559-46F5 strain easily changes in properties. However, a mutant derived from the MI559-46F5 strain (e.g., a natural mutant or an artificial mutant obtained through a mutagenic treatment with UV, X-ray, radiation, or chemicals), a zygote of the strain, and a recombinant of the strain are also encompassed in the present invention as long as they are capable of producing the compound represented by the Structural Formula (A).

(Compound-Containing Composition)

A compound-containing composition of the present invention includes the compound represented by the Structural Formula (A), a salt thereof, or both thereof; and, if necessary, further includes other ingredients.

<Compound Represented by Structural Formula (A)>

An amount of the compound represented by the Structural Formula (A) contained in the compound-containing composition is not particularly limited and may be appropriately selected depending on the intended purpose. The compound-containing composition may be the compound represented by the Structural Formula (A) itself.

<Other Ingredients>

The other ingredients are not particularly limited and may be appropriately selected from pharmacologically acceptable carriers depending on the intended purpose. Examples thereof include an additive, an auxiliary agent, and water. These may be used alone or in combination.

The additive or the auxiliary agent is not particularly limited and may be appropriately selected depending on the intended purpose. Examples thereof include a disinfectant, a preserving agent, a binder, a thickener, an adhesive agent, a bonding agent, a colorant, a stabilizer, a pH adjuster, a buffer, a tonicity agent, a solvent, an antioxidant, a UV rays-preventing agent, a preventing agent for precipitation of crystals, a defoaming agent, a property-improving agent and an antiseptic agent.

The disinfectant is not particularly limited and may be appropriately selected depending on the intended purpose. Examples thereof include cationic surfactants such as benzalkonium chloride, benzethonium chloride, and cetylpyridinium chloride.

The preserving agent is not particularly limited and may be appropriately selected depending on the intended purpose. Examples thereof include p-hydroxybenzoate esters, chlorobutanol, and cresol.

The binder, thickener, and adhesive agent are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyl cellulose, hydroxypropylmethyl cellulose, carboxymethyl starch, pullulan, sodium alginate, ammonium alginate, propylene glycol alginate esters, guar gum, locust bean gum, gum Arabic, xanthan gum, gelatin, casein, polyvinyl alcohol, polyethylene oxide, polyethylene glycol, ethylene/propylene block polymers, sodium polyacrylate and polyvinylpyrrolidone.

The bonding agent is not particularly limited and may be appropriately selected depending on the intended purpose. Examples thereof include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate, and polyvinylpyrrolidone.

The colorant is not particularly limited and may be appropriately selected depending on the intended purpose. Examples thereof include titanium oxide and iron oxide.

The stabilizer is not particularly limited and may be appropriately selected depending on the intended purpose. Examples thereof include tragacanth, gum Arabic, gelatin, sodium pyrosulfite, EDTA, thioglycolic acid, and thiolactic acid.

The pH adjuster and the buffer are not particularly limited and may be appropriately selected depending on the intended purpose. Examples thereof include sodium citrate, sodium acetate, and sodium phosphate.

The tonicity agent is not particularly limited and may be appropriately selected depending on the intended purpose. Examples thereof include sodium chloride and glucose.

An amount of the other ingredients contained in the compound-containing composition is not particularly limited and may be appropriately selected depending on the intended purpose, as long as it does not impair effects of the compound represented by the Structural Formula (A).

<Application>

The compound-containing composition contains the compound represented by the Structural Formula (A), a salt thereof, or both thereof. Therefore, the compound-containing composition has an excellent prostaglandin production inhibitory action and high safety, and can be suitably used for the below-described prostaglandin production inhibitor of the present invention.

(Prostaglandin Production Inhibitor)

A prostaglandin production inhibitor of the present invention contains the compound-containing composition of the present invention; and, if necessary, further contains other ingredients. The prostaglandin production inhibitor has a prostaglandin production inhibitory action.

<Compound-Containing Composition>

An amount of the compound-containing composition contained in the prostaglandin production inhibitor is not particularly limited and may be appropriately selected depending on the intended purpose. The prostaglandin production inhibitor may be the compound-containing composition itself.

<Other Ingredients>

The other ingredients are not particularly limited and may be appropriately selected depending on the intended purpose. For example, the other ingredients may be the same as the other ingredients described for the compound-containing composition.

An amount of the other ingredients contained in the prostaglandin production inhibitor is not particularly limited and may be appropriately selected depending on the intended purpose, as long as it does not impair effects of the compound represented by the Structural Formula (A).

Note that, the prostaglandin production inhibitor may be used alone, or in combination with pharmaceuticals containing other active ingredients. The prostaglandin production inhibitor may be used in a state in which it is incorporated in the pharmaceuticals containing other active ingredients.

<Prostaglandin Production Inhibitory Action>

A method for determining the prostaglandin production inhibitory action is not particularly limited and may be appropriately selected from known methods depending on the intended purpose. For example, the method described in the following Test Example may be used.

<Dosage Form>

The dosage form of the prostaglandin production inhibitor is not particularly limited and may be appropriately selected depending on the intended purpose. Examples thereof include a solid preparation, a semi-solid preparation, and a liquid preparation.

—Solid Preparation—

The solid preparation is not particularly limited and may be appropriately selected depending on the intended purpose. In the case where it is used internally, examples thereof include tablets, chewable tablets, foaming tablets, orally-disintegrating tablets, troches, drops, hard capsules, soft capsules, granules, powder, pills, dry syrups and infusions.

In the case where it is used externally, examples thereof include suppositories, cataplasms, and plasters.

—Semi-Solid Preparation—

The semi-solid preparation is not particularly limited and may be appropriately selected depending on the intended purpose. In the case where it is used internally, examples thereof include electuaries, chewing gums, whip, and jelly.

In the case where it is used externally, examples thereof include ointments, creams, mousse, inhaler, and nasal gel.

—Liquid Preparation—

The liquid preparation is not particularly limited and may be appropriately selected depending on the intended purpose. In the case where it is used internally, examples thereof include syrups, drinks, suspensions, and spirits.

In the case where it is used externally, examples thereof include solutions, eye drops, aerosol, and sprays.

<Administration>

Regarding the prostaglandin production inhibitor, the administration method, the administration dose, the timing of administration and the subject to be administered are not particularly limited and may be appropriately selected depending on the intended purpose.

The administration method is not particularly limited and may be appropriately selected depending on the intended purpose. Examples thereof include a local administration method, an enteric administration method, and a parenteral administration method.

The administration dose is not particularly limited and may be appropriately selected considering various factors of the subject to be administered, such as the age, body weight, constitution, symptom and the presence or absence of administration of pharmaceuticals containing other active ingredients.

The animal species serving as the subject to be administered is not particularly limited and may be appropriately selected depending on the intended purpose. Examples of thereof include human, monkey, pig, bovine, sheep, goat, dog, cat, mouse, rat and bird. Among them, human is suitably used.

<Application>

The prostaglandin production inhibitor has an excellent prostaglandin production inhibitory action and high safety. Therefore, it can inhibit physiological responses caused by prostaglandin such as inflammation reactions (e.g., pruritus, fever, vascular hyperpermeability, and pain), abnormal enhancement of sensory nerve, bronchial smooth muscle contraction, platelet aggregation, tumor-cell proliferation, bone resorption promotion, and neuron degeneration; and it can be suitably used as a prophylactic agent or a therapeutic agent of various diseases such as asthma, a cardiovascular disease, preterm delivery, nephritis, atherosclerosis, overactive bladder, chronic rheumatoid arthritis, osteoarthritis, and cancer.

EXAMPLES

The present invention now will be described in more detail by way of Examples, which should not be construed as limiting the present invention thereto. Note that, in the following Examples, "%" means "% by mass," unless otherwise stated.

Production Example 1

<Culturing Step>

A liquid medium for a seed culture liquid (the pH of the medium being adjusted to 7.0) was prepared by suspending into water galactose 2%, dextrin 2%, glycerin 1%, BACTO SOYTONE (manufactured by Difco Co., Ltd.) 1%, corn steep liquor 0.5%, ammonium sulfate 0.2% and calcium carbonate 0.2%. The resultant liquid medium for a seed culture liquid was dispensed into 500 mL-conical flasks so that each conical flask contained 110 mL of the liquid medium, followed by routinely sterilizing at 120° C. for 20 min.

Microorganisms of *Saccharothrix* sp. MI559-46F5 strain deposited under accession number NITE BP-01152 which had been precultured in an agar slant medium was inoculated in the sterilized liquid medium for a seed culture liquid, followed by shake-culturing (180 rpm) at 30° C. for 2 days, to thereby obtain a seed culture liquid.

Then, a liquid medium for a production medium (the pH of the medium being adjusted to 7.0) was prepared by suspending into water glycerin 2.0%, dextrin 2.0%, yeast extract (manufactured by Wako Pure Chemical Industries, Ltd.) 0.3%, BACTO SOYTONE (manufactured by Difco Co., Ltd.) 1.0%, ammonium sulfate 0.2% and calcium carbonate 0.2%. The resultant liquid medium for a production medium was dispensed into 500 mL-conical flasks so that each conical flask contained 110 mL of the liquid medium, followed by routinely sterilizing at 120° C. for 20 min. Two percent by volume of the above-prepared seed culture liquid was inoculated in the liquid medium for a production medium, followed by shake-culturing (180 rpm) for 5 days at 27° C.

<Isolation Step>

The culture liquid obtained from the culturing step (15 L) was centrifuged at 8,000 rpm for 15 min to thereby separate into a culture filtrate and a microbial body. Then, the resultant culture filtrate was allowed to pass through a column (internal diameter: 80 mm, length: 300 mm) filled with 1.5 L of an adsorptive resin (DIAION (registered trademark) HP-20, manufactured by Mitsubishi Chemical Corporation) equilibrated with water. Thereafter, the adsorptive resin was washed with 3 L of water, and then with 4.5 L of a 50% by volume methanol solution in water. Then, the washed adsorptive resin was eluted with 3 L of methanol to thereby obtain an eluate. Methanol was distilled off with an evaporator from the resultant eluate. The resultant residue was dissolved into 1.5 L of water. To this, 1.5 L of ethyl acetate was added and stirred, followed by leaving to stand to thereby separate into 2 phases. The resultant ethyl acetate phase was collected and washed. The above-described washing procedure was further repeated twice. Then, ethyl acetate was distilled off with an evaporator to thereby yield 1.13 g of red oil.

The resultant red oil was dissolved into a small amount of methanol, followed by applying to CELITE. The CELITE was added to a 140 mL-silica gel column filled with chloroform, followed by washing with 0.8 L of chloroform, 0.8 L of a chloroform-methanol mixed solution (100:1 (volume ratio)), and 1.2 L of a chloroform-methanol mixed solution (100:2 (volume ratio)), and eluting with 1.2 L of a chloroform-methanol mixed solution (10:1 (volume ratio)). The resultant eluate was concentrated under a reduced pressure to thereby yield 127.6 mg of red oil.

The red oil was dissolved into methanol, followed by allowing to pass through a column (TOYOPEARL HW-40F, internal diameter: 37 mm, length: 670 mm, manufactured by TOSOH CORPORATION) and eluting with methanol. The resultant eluate was collected and concentrated under a reduced pressure to thereby yield reddish violet oil. The reddish violet oil was dissolved into a small amount of methanol, followed by subjecting to a C18 reverse phase column chromatography (CAPCELL PAK UG120, internal diameter: 20 mm, length: 250 mm, manufactured by Shiseido Company, Limited) using a developing solvent of acetonitrile/water/trifluoroacetic acid (20:80:0.0001 (volume ratio)) at a flow rate of 8 mL/min. The resultant was concentrated under a reduced pressure to thereby yield 31.8 mg of a target substance.

Test Example 1

Identification of Compound

The target substance obtained from Production Example 1 was measured for physico-chemical properties. The physico-chemical properties are described below. Therefore, it was confirmed that the target substance was a novel compound having a structure represented by the following Structural Formula (A).
(1) Appearance: reddish violet powder
(2) Molecular formula: $C_{20}H_{24}N_2O_9$
(3) High resolution mass spectrometry (HRESIMS: positive ion mode)
   Found: m/z 459.1371 $(M+Na)^+$
   Calcd: m/z 459.1374 (as $C_{20}H_{24}N_2O_9Na$)
(4) Specific rotation $[\alpha]D^{23}=-358°$ (c 0.0036, methanol)
(5) Infrared absorption spectrum measured by the KBr method: as shown in FIG. 1
(6) UV absorption spectrum measured in methanol: as shown in FIG. 2
   $\lambda_{max}$ nm ($\epsilon$): 263 (9,909), 470 (2,739)
(7) Proton nuclear magnetic resonance (NMR) spectrum measured at 600 MHz in deuterated dimethyl sulfoxide (deuterated DMSO) at 25° C.: as shown in FIG. 3
(8) $^{13}C$ nuclear magnetic resonance spectrum measured at 150 MHz in deuterated DMSO at 25° C.: as shown in FIG. 4

Structural Formula (A)

In the following Test Examples 2 to 4, the compound represented by the Structural Formula (A) was used as a test substance and subjected to the following test.

Test Example 2

$PGE_2$ Production Inhibitory Action

The compound represented by the Structural Formula (A) was evaluated for a $PGE_2$ production inhibitory action as follows.
—Culturing of SW982 Cell—
A SW982 cell which is a human osteosarcoma cell line (purchased from ATCC (American Type Culture Collection)) was suspended into DMEM/F12 (Dulbecco's Modified Eagle Medium: Nutrient Mixture F-12, manufactured by Thermo Fisher Scientific) containing 10% fetal bovine serum (manufactured by Nichirei Corporation), followed by inoculating into a 96-well culture plate at $1 \times 10^4$ cells/well and incubating overnight.
—Measurement of $PGE_2$ Concentration in System Containing Test Substance—
After the incubation overnight, the medium in the 96-well culture plate containing the SW982 cells was replaced with HEPES-HANKS buffer (manufactured by NISSUI PHARMACEUTICAL CO., LTD.). Then, the test substance produced in Production Example 1 (the compound represented by the Structural Formula (A)) was added to each well at 10,000 ng/mL, 3,333 ng/mL, 1,111 ng/mL, 370 ng/mL, 123 ng/mL, 41 ng/mL, 14 ng/mL, 5 ng/mL, or 2 ng/mL. Bradykinin serving as an inflammatory stimulating agent (manufactured by PEPTIDE INSTITUTE, INC.) was further added to the each well at 1 nM. After incubating for 30 min, a culture supernatant was collected, followed by measuring a $PGE_2$ concentration A in the culture supernatant using a kit based on a HTRF (Homogeneous Time-Resolved Fluorescence) method (62P2APEB, manufactured by Cisbio Bioassays).
—Measurement of $PGE_2$ Concentration in Negative Control—
As a negative control, a $PGE_2$ concentration B was measured in the same manner as in the measurement of the $PGE_2$ concentration in the system containing the test substance, except that neither the test substance nor bradykinin (inflammatory stimulating agent) was added.
—Measurement of $PGE_2$ Concentration in Positive Control—
As a positive control, a $PGE_2$ concentration C was measured in the same manner as in the measurement of the $PGE_2$ concentration in the system containing the test substance, except that the test substance was not added.
—Calculation of $PGE_2$ Production Rate—
Based on the measurement result of $PGE_2$ concentration in the each well, a $PGE_2$ production rate was calculated according to the following Expression (1):

$PGE_2$ production rate (%)=$(A-B)/(C-B) \times 100$   Expression (1)

Figure 5:
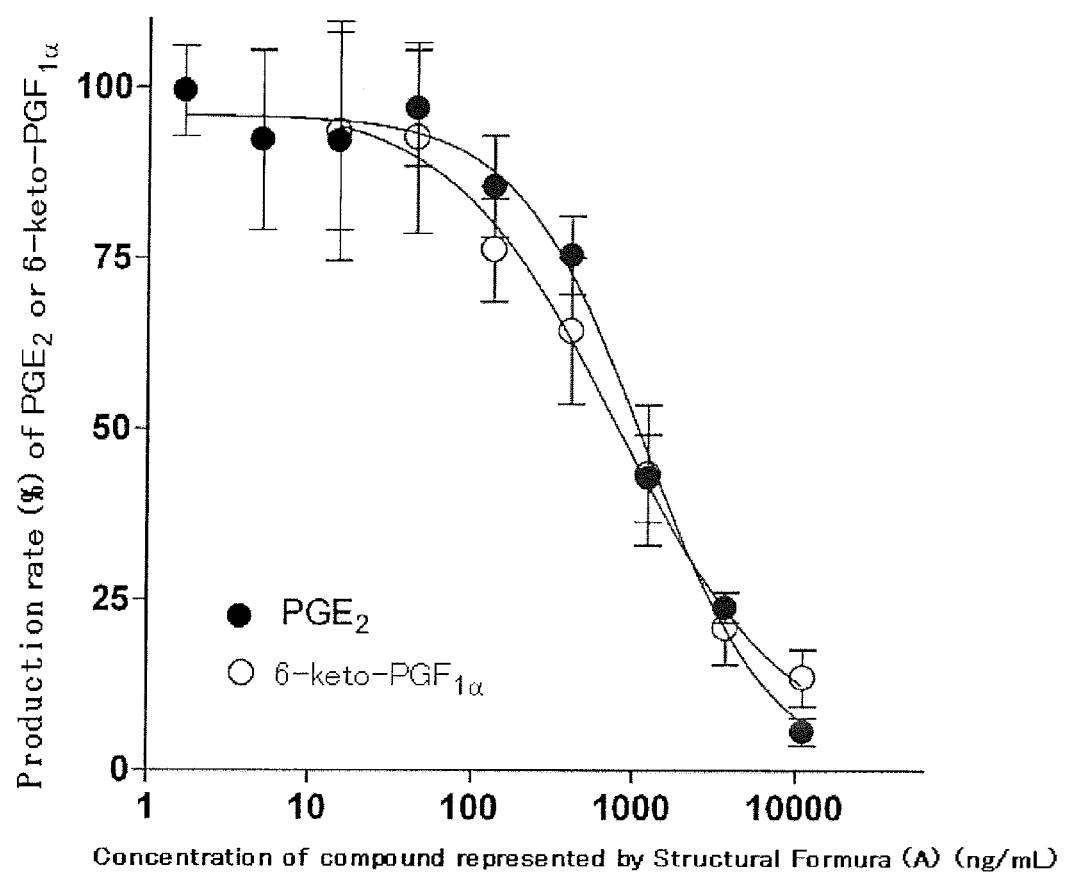
FIG. 5 is a graph of a prostaglandin production inhibitory action exhibited by a compound of the present invention, where the vertical axis: production rates (%) of $PGE_2$ or 6-keto-$PFG_{1\alpha}$ and the horizontal axis: concentrations of the compound (μg/mL).

In the Expression (1),
A denotes a $PGE_2$ concentration in the system containing the test substance,
B denotes a $PGE_2$ concentration in the negative control, and
C denotes a $PGE_2$ concentration in the positive control.
Results are shown in FIG. 5. In Test Example 2, in the case where the test substance contains a substance effective for inhibiting prostaglandin production, an amount of $PGE_2$ detected in the cell culture liquid is decreased. That is, the $PGE_2$ production rate is decreased.

As a result of adding the compound represented by the Structural Formula (A) as the test substance, the $PGE_2$ production rate was decreased, as shown in FIG. 5.

Accordingly, the compound represented by the Structural Formula (A) was confirmed to have an excellent prostaglandin production inhibitory action.

Test Example 3

$PGI_2$ Production Inhibitory Action

The compound represented by the Structural Formula (A) was evaluated for a $PGI_2$ production inhibitory action as follows. $PGI_2$ is metabolized to 6-keto-$PGF_{1\alpha}$ (6-keto-prostaglandin $F_{1\alpha}$) which is a stabilized metabolite. Therefore, a concentration of $PGI_2$ produced can be determined by measuring a concentration of 6-keto-$PGF_{1\alpha}$.

—Culturing of SW982 Cell—

A SW982 cell which is human osteosarcoma cell line (purchased from ATCC) was suspended into DMEM/F12 (manufactured by Thermo Fisher Scientific) containing 10% fetal bovine serum (manufactured by Biowest), followed by inoculating into a 96-well culture plate at $1 \times 10^4$ cells/well and incubating overnight.

—Measurement of 6-Keto-$PGF_{1\alpha}$ Concentration in System Containing Test Substance—

After the incubation overnight, the medium in the 96-well culture plate containing the SW982 cells was replaced with HEPES-HANKS buffer (manufactured by NISSUI PHARMACEUTICAL CO., LTD.). Then, the test substance produced in Production Example 1 (the compound represented by the Structural Formula (A)) was added to each well at 10,000 ng/mL, 3,333 ng/mL, 1,111 ng/mL, 370 ng/mL, 123 ng/mL, 41 ng/mL, or 14 ng/mL. Bradykinin serving as an inflammatory stimulating agent (manufactured by PEPTIDE INSTITUTE, INC.) was further added to the each well at 1 nM. After incubating for 30 min, a culture supernatant was collected, followed by measuring a 6-keto-$PGF_{1\alpha}$ concentration D in the culture supernatant using a 6-keto Prostaglandin F1α enzyme immunoassay kit (#515211, manufactured by Cayman Chemical Company).

—Measurement of 6-Keto-$PGF_{1\alpha}$ Concentration in Negative Control—

As a negative control, a 6-keto-$PGF_{1\alpha}$ concentration E was measured in the same manner as in the measurement of the 6-keto-$PGF_{1\alpha}$ concentration in the system containing the test substance, except that neither the test substance nor bradykinin (inflammatory stimulating agent) was added.

—Measurement of 6-Keto-$PGF_{1\alpha}$ Concentration in Positive Control—

As a positive control, a 6-keto-$PGF_{1\alpha}$ concentration F was measured in the same manner as in the measurement of the 6-keto-$PGF_{1\alpha}$ concentration in the system containing the test substance, except that the test substance was not added.

—Calculation of 6-Keto-$PGF_{1\alpha}$ Production Rate—

Based on the measurement result of 6-keto-$PGF_{1\alpha}$ concentration in the each well, a 6-keto-$PGF_{1\alpha}$ production rate was calculated according to the following Expression (2):

$$\text{6-keto-PGF}_{1\alpha} \text{ production rate (\%)} = (D-E)/(F-E) \times 100 \quad \text{Expression (2)}$$

In the Expression (2),

D denotes a 6-keto-$PGF_{1\alpha}$ concentration in the system containing the test substance, E denotes a 6-keto-$PGF_{1\alpha}$ concentration in the negative control, and F denotes a 6-keto-$PGF_{1\alpha}$ concentration in the positive control.

Results are shown in FIG. 5. In Test Example 3, in the case where the test substance contains a substance effective for inhibiting prostaglandin production, $PGI_2$ production in the cell culture liquid is inhibited. Therefore, an amount of 6-keto-$PGF_{1\alpha}$, which is a stabilized metabolite of $PGI_2$, detected in the cell culture liquid is decreased. That is, the 6-keto-$PGF_{1\alpha}$ production rate is decreased.

As a result of adding the compound represented by the Structural Formula (A) as the test substance, the 6-keto-$PGF_{1\alpha}$ production rate was decreased, as shown in FIG. 5.

Accordingly, the compound represented by the Structural Formula (A) was confirmed to have an excellent prostaglandin production inhibitory action.

Test Example 4

Cytotoxicity Test

The compound represented by the Structural Formula (A) was evaluated for cytotoxicity as follows.

—Measurement of the Number of Cells in System Containing Test Substance—

A SW982 cell (purchased from ATCC) at $2 \times 10^3$ cells/well was prepared with DMEM/F12 medium (manufactured by Thermo Fisher Scientific) containing 10% fetal bovine serum (manufactured by Nichirei Corporation), followed by inoculating into a 96-well culture plate so that each well contained 0.1 mL. At the same time, the test substance produced in Production Example 1 (the compound represented by the Structural Formula (A)) was added to each well at a concentration described in the following Table 1, followed by incubating for 48 hours under a condition of 37° C. and 5% $CO_2$. After the incubation for 48 hours, 10 μL of a cytometric kit (CELL COUNTING KIT-8, manufactured by DOJINDO LABORATORIES) was added to the each well, followed by incubating for 2 hours. Then, an absorbance at 450 nm G was measured.

—Calculation of Cell Proliferation Rate—

The cytometric kit allows living cells to develop a color. Accordingly, the higher absorbance at 450 nm is, the larger the number of living cells is, that is, cell proliferation is not affected. Therefore, based on the measurement result of absorbance in the each well, a cell proliferation rate was calculated according to the following Expression (3) to thereby evaluate an influence upon the cell proliferation:

$$\text{Cell proliferation rate (\%)} = G/H \times 100 \quad \text{Expression (3)}$$

In the Expression (3),

G denotes an absorbance at 450 nm in the system containing the test substance, and H denotes an absorbance at 450 nm in the system containing no test substance (i.e., at a concentration of 0 nM in the following Table 1).

TABLE 1

| Concentration (nM) | Cell proliferation rate (%) |
|---|---|
| 30,000 | 95 |
| 10,000 | 111 |
| 333 | 103 |
| 111 | 100 |
| 0 | 100 |

As a result of adding the compound represented by the Structural Formula (A) as the test substance, the compound represented by the Structural Formula (A) was confirmed not to affect cell proliferation of the SW982 cell and to have high safety, as shown in Table 1.

Embodiments of the present invention are as follows.

<1> A compound represented by the following Structural Formula (A) or a salt thereof:

Structural Formula (A)

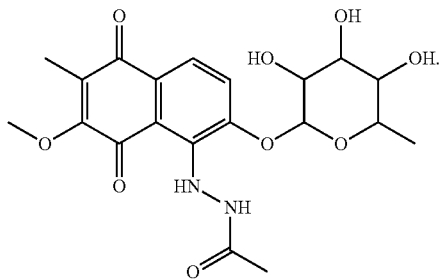

<2> A method for producing a compound represented by the following Structural Formula (A), including:
culturing a microorganism belonging to the genus *Saccharothrix* and capable of producing the compound represented by the following Structural Formula (A); and
isolating the compound represented by the following Structural Formula (A) from a culture obtained from the culturing:

Structural Formula (A)

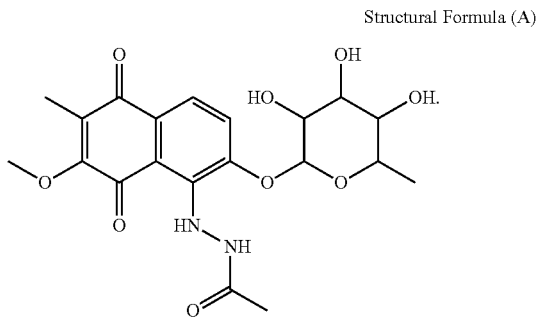

<3> The method according to <2>, wherein the microorganism belonging to the genus *Saccharothrix* and capable of producing the compound represented by the Structural Formula (A) is a microorganism of *Saccharothrix* sp. MI559-46F5 strain deposited under accession number NITE BP-01152.

<4> A microorganism belonging to the genus *Saccharothrix* and capable of producing a compound represented by the following Structural Formula (A):

Structural Formula (A)

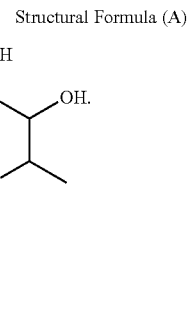

<5> The microorganism according to <4>, wherein the microorganism is a microorganism of *Saccharothrix* sp. MI559-46F5 strain deposited under accession number NITE BP-01152.

<6> A compound-containing composition, including:
a compound represented by the following Structural Formula (A), a salt thereof, or both thereof:

Structural Formula (A)

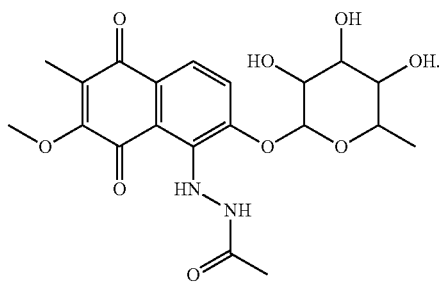

<7> A prostaglandin production inhibitor, including:
the compound-containing composition according to <6>,
wherein the prostaglandin production inhibitor has a prostaglandin production inhibitory action.

Accession Number
NITE BP-01152

INDUSTRIAL APPLICABILITY

A compound of the present invention has an excellent prostaglandin production inhibitory action and high safety. Therefore, it can inhibit physiological responses caused by prostaglandin such as inflammation reactions (e.g., pruritus, fever, vascular hyperpermeability, and pain), abnormal enhancement of sensory nerve, bronchial smooth muscle contraction, platelet aggregation, tumor-cell proliferation, bone resorption promotion, and neuron degeneration; and it can be suitably used as an active ingredient of a prophylactic agent or a therapeutic agent of various diseases such as asthma, a cardiovascular disease, preterm delivery, nephritis, atherosclerosis, overactive bladder, chronic rheumatoid arthritis, osteoarthritis, and cancer.

What is claimed is:
1. A method for producing a compound represented by the following Structural Formula (A), comprising:
culturing a microorganism belonging to the genus *Saccharothrix* and capable of producing a compound represented by the following Structural Formula (A); and
isolating the compound represented by the following Structural Formula (A) from a culture obtained from the culturing:

Structural Formula (A)

2. The method according to claim 1, wherein the microorganism belonging to the genus *Saccharothrix* and capable of producing a compound represented by the Structural Formula (A) is a microorganism of *Saccharothrix* sp. MI559-46F5 strain deposited under accession number NITE BP-01152.

* * * * *